United States Patent
Nour et al.

(10) Patent No.: US 12,259,377 B2
(45) Date of Patent: Mar. 25, 2025

(54) DETECTING HYDROCARBON FUELS IN LUBRICATION OILS

(71) Applicant: Saudi Arabian Oil Company, Dhahran (SA)

(72) Inventors: Maha Nour, Thuwal (SA); Amjad Felemban, Thuwal (SA); Hamad Al Saiari, Al-Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 534 days.

(21) Appl. No.: 17/713,640

(22) Filed: Apr. 5, 2022

(65) Prior Publication Data
US 2023/0314402 A1    Oct. 5, 2023

(51) Int. Cl.
G01N 33/28    (2006.01)
B01L 3/00    (2006.01)

(52) U.S. Cl.
CPC .... G01N 33/2841 (2013.01); B01L 3/502715 (2013.01); *B01L 2300/0851* (2013.01); *B01L 2300/0858* (2013.01)

(58) Field of Classification Search
CPC ........... G01N 33/2841; B01L 3/502715; B01L 2300/0851; B01L 2300/0858
USPC ......................................................... 73/833
See application file for complete search history.

(56) References Cited

U.S. PATENT DOCUMENTS

| | | |
|---|---|---|
| 3,156,644 A | 11/1964 | Kunin |
| 4,031,398 A | 6/1977 | Callis et al. |
| 4,307,061 A | 12/1981 | Sarholz |
| 4,651,010 A | 3/1987 | Javan |
| 5,422,719 A | 6/1995 | Goldstein |
| 5,818,582 A | 10/1998 | Fernandez et al. |
| 5,899,567 A | 5/1999 | Morris, Jr. |
| 5,982,847 A | 11/1999 | Nelson |
| 6,023,961 A | 2/2000 | Discenzo |

(Continued)

FOREIGN PATENT DOCUMENTS

| FR | 2817346 | 5/2002 |
|---|---|---|
| WO | WO 2020047469 | 3/2020 |

OTHER PUBLICATIONS

Nunes et al., "Cyclic olefin polymers: emerging materials for lab-on-a-chip applications", Microfluid Nanofluid 9: 145-161 (Year: 2010).*

(Continued)

*Primary Examiner* — Nathaniel T Woodward
(74) *Attorney, Agent, or Firm* — Fish & Richardson P.C.

(57) ABSTRACT

An apparatus includes a plate and a micro-protrusion baffle. The plate defines a microfluidic channel that is configured to flow a sample of lubrication oil. The microfluidic channel has an inlet for receiving the sample of lubrication oil. The microfluidic channel has an outlet for discharging the sample of lubrication oil. The plate defines walls of the microfluidic channel. The walls extend from the inlet to the outlet. The micro-protrusion baffle is located within the microfluidic channel between the inlet and the outlet. The micro-protrusion baffle extends from any of the walls. The micro-protrusion baffle includes a cyclic olefin copolymer. Dissolution of at least a portion of the micro-protrusion baffle in response to the sample of lubrication oil flowing through the microfluidic channel indicates a presence of hydrocarbon fuel in the sample of lubrication oil.

20 Claims, 5 Drawing Sheets

(56) References Cited

U.S. PATENT DOCUMENTS

| | | | |
|---|---|---|---|
| 6,507,401 | B1 | 1/2003 | Turner |
| 6,525,325 | B1 | 2/2003 | Andrews et al. |
| 6,692,720 | B1 | 2/2004 | Ninane et al. |
| 6,707,556 | B2 | 3/2004 | Turner |
| 6,911,830 | B2 | 6/2005 | Heremans et al. |
| 7,442,291 | B1 | 10/2008 | Discenzo |
| 7,839,492 | B2 | 11/2010 | Parks, II et al. |
| 8,017,408 | B2 | 9/2011 | Meinhart et al. |
| 8,390,796 | B2 | 3/2013 | Honda |
| 8,408,073 | B2 | 4/2013 | Sparks et al. |
| 8,704,174 | B2 | 4/2014 | Ukon |
| 8,910,514 | B2 | 12/2014 | Sullivan et al. |
| 9,206,386 | B2 | 12/2015 | Tunheim et al. |
| 9,255,875 | B2 | 2/2016 | Denenberg et al. |
| 9,518,918 | B2 | 12/2016 | Mann et al. |
| 9,822,356 | B2 | 11/2017 | Ismagilov et al. |
| 10,060,899 | B2 | 8/2018 | Hegazi et al. |
| 10,100,966 | B2 | 10/2018 | Vermont et al. |
| 10,317,388 | B2 | 6/2019 | Hegazi et al. |
| 10,502,409 | B2 | 12/2019 | Meinhart et al. |
| 10,643,324 | B2 | 5/2020 | Al Shehri et al. |
| 10,677,775 | B2 * | 6/2020 | Molla ............... B01L 3/502753 |
| 10,768,094 | B2 | 9/2020 | Amer et al. |
| 10,908,069 | B2 | 2/2021 | Amer et al. |
| 2002/0158211 | A1 | 10/2002 | Gillispie |
| 2003/0133105 | A1 | 7/2003 | Gorelik et al. |
| 2003/0141459 | A1 | 7/2003 | Hegazi et al. |
| 2004/0007675 | A1 | 1/2004 | Gillispie et al. |
| 2004/0124366 | A1 | 7/2004 | Zeng et al. |
| 2006/0114007 | A1 | 6/2006 | Cho |
| 2007/0009423 | A1 | 1/2007 | Handy et al. |
| 2007/0063140 | A1 | 3/2007 | Liu |
| 2007/0095395 | A1 | 5/2007 | Spiess |
| 2007/0187617 | A1 | 8/2007 | Kong |
| 2009/0006004 | A1 | 1/2009 | Sens et al. |
| 2009/0216419 | A1 | 8/2009 | Shaw |
| 2010/0269579 | A1 | 10/2010 | Lawrence et al. |
| 2011/0155925 | A1 | 6/2011 | Ukon |
| 2011/0166802 | A1 | 7/2011 | Kong |
| 2011/0236569 | A1 | 9/2011 | Weiller |
| 2011/0267603 | A1 | 11/2011 | Shaw |
| 2011/0303834 | A1 | 12/2011 | Hegazi et al. |
| 2012/0086942 | A1 | 4/2012 | Honda |
| 2013/0333893 | A1 | 12/2013 | Morris |
| 2014/0198313 | A1 | 7/2014 | Tracy et al. |
| 2015/0009495 | A1 | 1/2015 | Li et al. |
| 2015/0085290 | A1 | 3/2015 | Fjerdingstad |
| 2015/0168368 | A1 | 6/2015 | Hegazi et al. |
| 2016/0195509 | A1 | 7/2016 | Jamieson |
| 2016/0202194 | A1 | 7/2016 | Lees |
| 2016/0349198 | A1 | 12/2016 | Barney |
| 2018/0369778 | A1 * | 12/2018 | Tatoulian ............... B01J 19/249 |
| 2021/0255039 | A1 | 8/2021 | Morgan, III |
| 2021/0260585 | A1 * | 8/2021 | Alabi ............... B01L 3/502753 |

OTHER PUBLICATIONS

Aboaba et al., "Brain tumor quantification equation: Modeled on complete step response algorithm," International Conference on Computer and Communication Engineering (ICCCE 2012), Jul. 3-5, 2012, 988-991, 4 pages.

Al-Abdullah et al., "Flash points and volatility characteristics of gasoline/diesel blends," Fuel, Aug. 2015, 153:67-69, 3 pages.

Al-Samhan et al., "Evaluating scale deposition and scale tendency of effluent water mix with seawater for compatible injection water," Journal of Petroleum Exploration and Production Technology, Jun. 2020, 10(5):2105-2111, 7 pages.

Álvarez et al., "Prediction of Flash-Point Temperature of Alcohol/Biodiesel/Diesel Fuel Blends," Ind. Eng. Chem. Res., Apr. 2019, 58(16):6860-6869, 10 pages.

Beck et al., "Development and characterization of a mobile photoacoustic sensor for on-line soot emission monitoring in diesel exhaust gas," in Analytical and Bioanalytical Chemistry, Apr. 2003, 375(8):1136-1143, 8 pages.

Bedoui et al., "Design and electro-thermal analysis of a platinum micro heater for gas sensors," 13th Int. Multi-Conference Syst. Signals Devices, SSD 2016, 4:558-561, 4 pages.

Bernasconi et al., "Advanced pipeline vibroacoustic monitoring," Pressure Vessels and Piping Conference, Jul. 2013, 5, 7 pages.

Bhavani et al., "Diesel to Dual Fuel Conversion Process Development," Artic. Int. J. Eng. Technol., 2018, 7(3):306-310, 5 pages.

Bieler et al., "Calibration of the step response of a 70 GHz sampling oscilloscope using a novel optoelectronic technique," Conference on Precision Electromagnetic Measurements Digest, CPEM Jun. 8-13, 2008, 678-679, 2 pages.

Bridges et al., "Small-signal step response of laser amplifiers and measurement of CO2 laser linewidth, " IEEE Journal of Quantum Electronics, Nov. 1968, 4(11): 777-782, 6 pages.

Brueckner et al., "Tunable diode laser absorption spectroscopy as method of choice for non-invasive and automated detection of microbial growth in media fills," Talanta, May 2017, 167:21-29 9 pages.

Butler et al., "Prediction of Flash Points of Middle Distillates," Ind. Eng. Chem., Apr. 1956, 48(4):808-812, 5 pages.

Chan et al., "Size-controlled growth of CdSe nanocrystals in microfluidic reactors," Nano Lett., Feb. 2003, 3(2):199-201, 3 pages.

Chen et al., "3D-printed microfluidic devices: fabrication, advantages and limitations—a mini review," Analytical Methods, Aug. 2016, 8(31):6005-6012, Aug. 21, 2016, 8 pages.

Demirbas et al., "Diesel Fuel From Waste Lubricating Oil by Pyrolitic Distillation," Pet. Sci. Technol., 33(2): 129-138, Dec. 2015, 12 pages.

Fiorentin et al., "Effect of the finite memory length of a recorder in evaluating its frequency response of from step response," Instrumentation and Measurement Technology Conference, May 21-23, 2002, Proceedings of the 19th IEEE, 1: 787-791, 5 pages.

Foerster et al., "In situ monitoring of microfluidic distillation" Chemical Engineering Journal, 227: 13-21, 2013, 9 pages.

Ghosh et al., "A mass manufacturable thermoplastic based microfluidic droplet generator on cyclic olefin copolymer," Journal of Micromechanics and Microengineering, Apr. 2019, 29(5):055009, 10 pages.

Giordano et al., "Distilling small volumes of crude oil," Fuel, 285: 119072, Feb. 2021, 8 pages.

Gülüm et al., "Density, flash point and heating value variations of corn oil biodiesel-diesel fuel blends," Fuel Process. Technol., Jun. 2015, 134:456-464, 9 pages.

Hafeez et al., "Liquid fuel synthesis in microreactors," React. Chem. Eng., Aug. 2018, 3(4):414-432, 19 pages.

Hartman et al., "Distillation in microchemical systems using capillary forces and segmented flow," Lab Chip, Jul. 2009, 9(13): 1843-1849, 8 pages.

Hartman et al., "Multistep microchemical synthesis enabled by microfluidic distillation," Angew. Chemie—Int. Ed., 49(5): 899-903, Jan. 2010, 5 pages.

Hibara et al., "Microfluidic distillation utilizing micro-nano combined structure," Chem. Lett., Sep. 2008, 37(10): 1064-1065, 2 pages.

Hua et al., "Determination of sulfur-containing compounds in diesel oils by comprehensive two-dimensional gas chromatography with a sulfur chemiluminescence detector," in Journal of Chromatography A, Nov. 2003, 1019(1-2):101-109, 9 pages.

Jain et al., "Design and Simulation of Microfluidic Passive Mixer With Geometric Variation," International Journal of Research in Engineering and Technology, Feb. 2016, 5(2):55-58, 5 pages.

Jena et al., "Cyclic olefin copolymer based microfluidic devices for biochip applications: Ultraviolet surface grafting using 2-methacryloyloxyethyl phosphorylcholine," Biomicrofluidics, Mar. 2012, 6(1):012822, 13 pages.

Jena et al., "Micro fabrication of cyclic olefin copolymer (COC) based microfluidic devices," Microsystem Technologies, Feb. 2012, 18(2):159-166, 8 pages.

Jiménez et al., "Chemiluminescence detection systems for the analysis of explosives," J. Hazard. Mater., Jan. 2004, 106(1): 1-8, 8 pages.

(56) References Cited

OTHER PUBLICATIONS

Jinno et al., "Identification of polycyclic aromatic hydrocarbons in extracts of diesel particulate matter by supercritical fluid chromatography coupled with an ultraviolet multichannel detector," Analytical Chemistry, 1986, 58(13): 2696-2699, 4 pages.
Kan et al., "Scale Prediction for Oil and Gas Production," SPE Journal, Feb. 2012, 17(2):362-378, 17 pages.
Karnati et al., "Design of Micro-heaters Inspired by Space Filling Fractal Curves," Proc. 2019 IEEE Reg. 10 Symp. TENSYMP 2019, Aug. 2019, pp. 231-236, 6 pages.
Kimmich et al., "Fault detection for modern Diesel engines using signal- and process model-based methods," Control Engineering Practice, Feb. 2005, 13(2):189-203, 15 pages.
Kothare et al., "Microreactors for efficient on-chip fuel processing and hydrogen generation," Nanofabrication: Technologies, Devices, and Applications, Jan. 2005, 5592(19):241, 14 pages.
Kraus et al., "An integrated multiphase flow sensor for microchannels," Exp. Fluids, Jun. 2004, 36(6):819-832, 14 pages.
Lam et al., "Development of multistage distillation in a microfluidic chip," Lab Chip, 11(7):1311-1317, Apr. 2011, 7 pages.
Lam et al., "Towards an understanding of the effects of operating conditions on separation by microfluidic distillation," Chem. Eng. Sci., 66(10): 2098-2106, May 2011, 9 pages.
Lamonte et al., "Cyclic Olefin Copolymers," Advanced Materials & Processes, Mar. 2001, 159(3):33-36, 4 pages.
Li et al., "Isoelectric focusing in cyclic olefin copolymer microfluidic channels coated by polyacrylamide using a UV photografting method," Electrophoresis, Apr. 2005, 26(9):1800-1806, 7 pages.
Lin et al., "Integrated microfluidic reactors," Nano Today, Dec. 2009, 4(6):470-481, 12 pages.
Liu et al., "Micro-distillation system for formaldehyde concentration detection," Chem. Eng. J., 304: 419-425, Nov. 2016, 7 pages.
Ljubas et al., "Influence of engine oils dilution by fuels on their viscosity, flash point and fire point," NAFTA, 2010, 61(2):73-79, 7 pages.
McGann et al., "Lean fuel detection with nanosecond-gated laser-induced breakdown spectroscopy," Combustion and Flame, Feb. 2021, 224:209-218, 10 pages.
McGuire et al., "Detection of the aromatic molecule benzonitrile (c-C6H5CN) in the interstellar medium," Science, Jan. 2018, 359(6372):202-205, 5 pages.
Mehra et al., "Six-wafer combustion system for a silicon micro gas turbine engine," J. Microelectromechanical Syst., Dec. 2000, 9(4):517-527, 11 pages.
Mendonca et al., "Application of step response impedance spectroscopy for detection of skin irritation," Engineering in Medicine and Biology Society, Sep. 17-21, 2003; Proceedings of the 25th Annual International Conference of the IEEE, 4: 3215-3217, 3 pages.
mitsuichemicals.com [online], "APEL," 2020, retrieved on Feb. 14, 2022, retrieved from URL <https://jp.mitsuichemicals.com/en/special/apel/about/properties/>, 7 pages.
Mulrooney et al., "Detection of carbon dioxide emissions from a diesel engine using a mid-infrared optical fibre based sensor," Sensors Actuators, A Phys., May 2007, 136(1):104-110, 7 pages.
Nunes et al., "Cyclic olefin polymers: Emerging materials for lab-on-a-chip applications," Microfluidics and Nanofluidics, Apr. 2010, 9(2-3):145-161, 17 pages.
Olajire, "A review of oilfield scale management technology for oil and gas production," Journal of Petroleum Science and Engineering, Nov. 2015, 135:723-737, 45 pages.
Petermann, "Chapter 4: Intensity-Modulation Characteristics of Laser Diodes," Laser diode modulation and Noise, Kluwer Academic, 1991, 78-118, 41 pages.

Rowland et al., "The Automated Assessment of Ultrasound Scanner Lateral and Slice Thickness Resolution: Use of the Step Response," Ultrasound in Medicine & Biology, 35(9): 1525-1534, Sep. 2009, 10 pages.
Schuresko et al., "Carboxylation kinetics of hemoglobin and myoglobin: linear transient response to step perturbation by laser photolysis," Biophysical Journal, 24(1): 382-383, Oct. 1978, 2 pages.
Seo et al., "Continuous microfluidic reactors for polymer particles," Langmuir, Dec. 2005, 21(25):11614-11622, 9 pages.
Soud, "Downstream oil theft: countermeasures and good practices," Atlantic Council, May 2020, retrieved from URL <https://www.atlanticcouncil.org/wp-content/uploads/2020/05/AC_OilTheft-Final-1.pdf> 56 pages.
Spannhake et al., "High-temperature MEMS heater platforms: Long-term performance of metal and semiconductor heater materials," Sensors, Apr. 2006, 6(4):405-419, 15 pages.
Sumitomo Heavy Industries Process Equipment Co., Ltd., "Consider a mixing vessel as a huge viscometer." Accessed: Aug. 20, 2020. [Online]. Available: https://www.shi-pe.shi.co.jp/english/technology/mixing-lecture/004/index.html, 3 pages.
Taghizadeh-Alisaraei et al., "Fault detection of injectors in diesel engines using vibration time-frequency analysis," Applied Acoustics, Jan. 2019, 143:48-58, 11 pages.
thomassci.com [online], "Multi-Position Hot Plate Stirrer, "2022, retrieved Feb. 15, 2022, retrieved from URL <https://www.thomassci.com/Equipment/Hot-Plates/_/Multi-Position-Hot-Plate-Stirrer?q=Multi%20Position%20Hotplate%20Stirrer>, 2 pages.
Udonne, "A comparative study of recycling of used lubrication Oils using distillation, acid and activated charcoal with clay methods," Journal of Petroleum and Gas Engineering, 2(2): 12-19 , Feb. 2011, 8 pages.
Vahdati et al., "External corrosion detection of oil pipelines using fiber optics." Sensors 20.3, 684, Jan. 2020, 16 pages.
Van-Den-Begin et al., "Fast adsorption-desorption kinetics of hydrocarbons in silicalite-1 by the single-step frequency response method," Zeolites, 9(4): 287-292, Jul. 1989, 6 pages.
Wardzinska et al., "Step response sensitivity of VLSI interconnects," 17th IEEE Workshop on Signal and Power Integrity (SPI), May 12-15, 2013, 4 pages.
Wronski et al., "The step response: a method to characterize mechanisms of renal blood flow autoregulation," American Journal of Physiology—Renal Physiology, Sep. 3, 2003, 285(4): F758-764, 7 pages.
Yamagata et al., "Synthesis of highly fluorescent diketopyrrolopyrrole derivative and two-step response of fluorescence to acid," Tetrahedron Letters, Mar. 24, 2010, 51(12): 1596-1599, 4 pages.
Yang et al., "Determination of sulfur compounds in catalytic diesel oil by gas chromatography with atomic emission detector and its applications," Se Pu, Nov. 2002, Abstract, 2 pages.
Youn et al., "Fabrication of micro mold for hot-embossing of polyimide microfluidic platform by using electron beam lithography combined with inductively coupled plasma," Microelectron. Eng., 2008, 85( 5-6):918-921, 4 pages.
Yu et al., "A novel polyimide based micro heater with high temperature uniformity," Sensors Actuators, A Phys., Feb. 2017, 257:58-64, 7 pages.
Zhang et al., ", "Design of the microfluidic chip of oil detection," Applied Mechanics and Materials, 117-119: 517-520, 2012, 5 pages.
Zhang et al., "Spray model based on step response theory," Fuel, May 2012, 95(1): 499-503, 5 pages.
Zhao et al., "Design principles and fabrication method for a miniaturized fuel gas combustion reactor," Sensors, The 3rd Conference on MicroFluidic Handling Systems, Oct. 2017, 4 pages.

* cited by examiner

DETECTING HYDROCARBON FUELS IN LUBRICATION OILS

TECHNICAL FIELD

This disclosure relates to detection of hydrocarbon fuels in lubrication oils.

BACKGROUND

Fuel smuggling is unfortunately a lucrative illegal act that is committed in various parts of the world. In some cases, fuels are transported to neighboring countries through illegal means. In some cases, fuels are diluted to increase volume in generating an increased profit. Sometimes petroleum products are diluted at the midstream level and transported downstream for sale to avoid detection of such dilution. In other cases, fuels are mixed with and hidden in other products to avoid detection of smuggling.

SUMMARY

This disclosure describes technologies relating to microfluidic devices that can be used to detect hydrocarbon fuels in lubrication oils. Certain aspects of the subject matter described can be implemented as a microfluidic apparatus. The microfluidic apparatus includes a plate and micro-protrusion baffles. The plate defines a microfluidic channel that is configured to flow lubrication oil. The microfluidic channel has an inlet for receiving the lubrication oil. The microfluidic channel has an outlet for discharging the lubrication oil. The plate defines walls of the microfluidic channel. The walls extend from the inlet to the outlet. The micro-protrusion baffles are located within the microfluidic channel. The micro-protrusion baffles are distributed between the inlet and the outlet. Each micro-protrusion baffle extends from any of the walls. Each micro-protrusion baffle includes a cyclic olefin copolymer that is insoluble in acyclic saturated hydrocarbons. Each micro-protrusion baffle is configured to at least partially dissolve in a presence of an aromatic hydrocarbon in the lubrication oil flowed through the microfluidic channel.

This, and other aspects, can include one or more of the following features. The walls can include a top wall, a bottom wall, a first side wall, and a second side wall. The bottom wall can be opposite the top wall. The second side wall can be opposite the first side wall. Each of the micro-protrusion baffles can extend from any of the first side wall or the second side wall. Each micro-protrusion baffle can extend from the bottom wall to the top wall. Each micro-protrusion baffle can include a free end that is a perpendicular distance, from the respective side wall from which the respective micro-protrusion baffle extends, that is in a range of from about 10 micrometers to about 100 micrometers. The micro-protrusion baffles, in a direction from the inlet to the outlet, can alternate between extending from the first side wall and extending from the second side wall. At least one of the micro-protrusion baffles can extend perpendicularly from the first side wall. Each micro-protrusion baffle can have a maximum dimension that is less than 1 millimeter. At least one of the micro-protrusion baffles can extend from the first side wall non-perpendicularly at a non-zero angle with respect to the first side wall. At least one of the micro-protrusion baffles can extend toward the outlet. At least one of the micro-protrusion baffles can extend toward the inlet.

Certain aspects of the subject matter described can be implemented as a method. A sample of lubrication oil is flowed through a microfluidic channel defined by a plate. The microfluidic channel has walls extending from an inlet to an outlet of the microfluidic channel. The sample of lubrication oil is flowed across micro-protrusion baffles that are located within the microfluidic channel. The micro-protrusion baffles are distributed between the inlet and the outlet. Each of the micro-protrusion baffles extend from any of the walls. Each of the micro-protrusion baffles include a cyclic olefin copolymer. It is detected that at least a portion of any of the micro-protrusion baffles has dissolved in response to the sample of lubrication oil flowing across the micro-protrusion baffles. A presence of hydrocarbon fuel in the sample of lubrication oil is determined based on detecting that at least a portion of any of the micro-protrusion baffles has dissolved.

This, and other aspects, can include one or more of the following features. The walls can include a top wall, a bottom wall, a first side wall, and a second side wall. The bottom wall can be opposite the top wall. The second side wall can be opposite the first side wall. Each of the micro-protrusion baffles can extend from any of the first side wall or the second side wall. Each of the micro-protrusion baffles can extend from the bottom wall to the top wall. Each of the micro-protrusion baffles can extend from any of the first side wall or the second side wall by a perpendicular distance from the respective side wall in a range of from about 10 micrometers to about 100 micrometers. The micro-protrusion baffles, in a direction from the inlet to the outlet, can alternate between extending from the first side wall and extending from the second side wall. At least one of the micro-protrusion baffles can extend perpendicularly from the first side wall. At least one of the micro-protrusion baffles can extend from the first side wall non-perpendicularly at a non-zero angle with respect to the first side wall. A second sample of lubrication oil can be flowed through the microfluidic channel. The second sample of lubrication oil can be flowed across the micro-protrusion baffles. It can be detected that the micro-protrusion baffles have not dissolved in response to the second sample of lubrication oil flowing across the micro-protrusion baffles. An absence of hydrocarbon fuel in the second sample of lubrication oil can be determined based on detecting that the micro-protrusion baffles have not dissolved.

Certain aspects of the subject matter described can be implemented as an apparatus. The apparatus includes a plate and a micro-protrusion baffle. The plate defines a microfluidic channel that is configured to flow a sample of lubrication oil. The microfluidic channel has an inlet for receiving the sample of lubrication oil. The microfluidic channel has an outlet for discharging the sample of lubrication oil. The plate defines walls of the microfluidic channel. The walls extend from the inlet to the outlet. The micro-protrusion baffle is located within the microfluidic channel between the inlet and the outlet. The micro-protrusion baffle extends from any of the walls. The micro-protrusion baffle includes a cyclic olefin copolymer. Dissolution of at least a portion of the micro-protrusion baffle in response to the sample of lubrication oil flowing through the microfluidic channel indicates a presence of hydrocarbon fuel in the sample of lubrication oil. In some implementations, the micro-protrusion baffle has a maximum dimension that is less than 1 millimeter and extends perpendicularly from one of the walls.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

This disclosure describes a microfluidic apparatus that can be used to detect the presence or absence of hydrocarbon fuels that may be hidden in lubrication oils. The microfluidic apparatus has a microfluidic channel with one or more micro-protrusion baffle located within the channel. The micro-protrusion baffle is made of a material that is insoluble in acyclic saturated hydrocarbons (typically present in lubrication oils) and soluble in aromatic hydrocarbons (typically present in hydrocarbon fuels). A sample of lubrication oil is flowed through the microfluidic channel and across the micro-protrusion baffle. Dissolution of at least a portion of the micro-protrusion baffle can indicate the presence of hydrocarbon fuel in the lubrication oil.

The subject matter described in this disclosure can be implemented in particular implementations, so as to realize one or more of the following advantages. The apparatus is small and portable (for example, having a total volume of less than 1 cubic feet), thus the apparatus can be used in various locations that use or transport lubrication oils. For example, the apparatus can be used in a laboratory, onsite at a pipeline, or onsite at a processing facility that uses lubrication oil. The apparatus can be used to quickly test a small sample of a lubrication oil to identify cases in which smugglers may be trying to smuggle hydrocarbon fuels by hiding them in the transport of lubrication oils. Thus, the apparatuses and methods described can be implemented to mitigate or prevent hydrocarbon fuel smuggling in a quick, reliable manner.

Figure 1A:
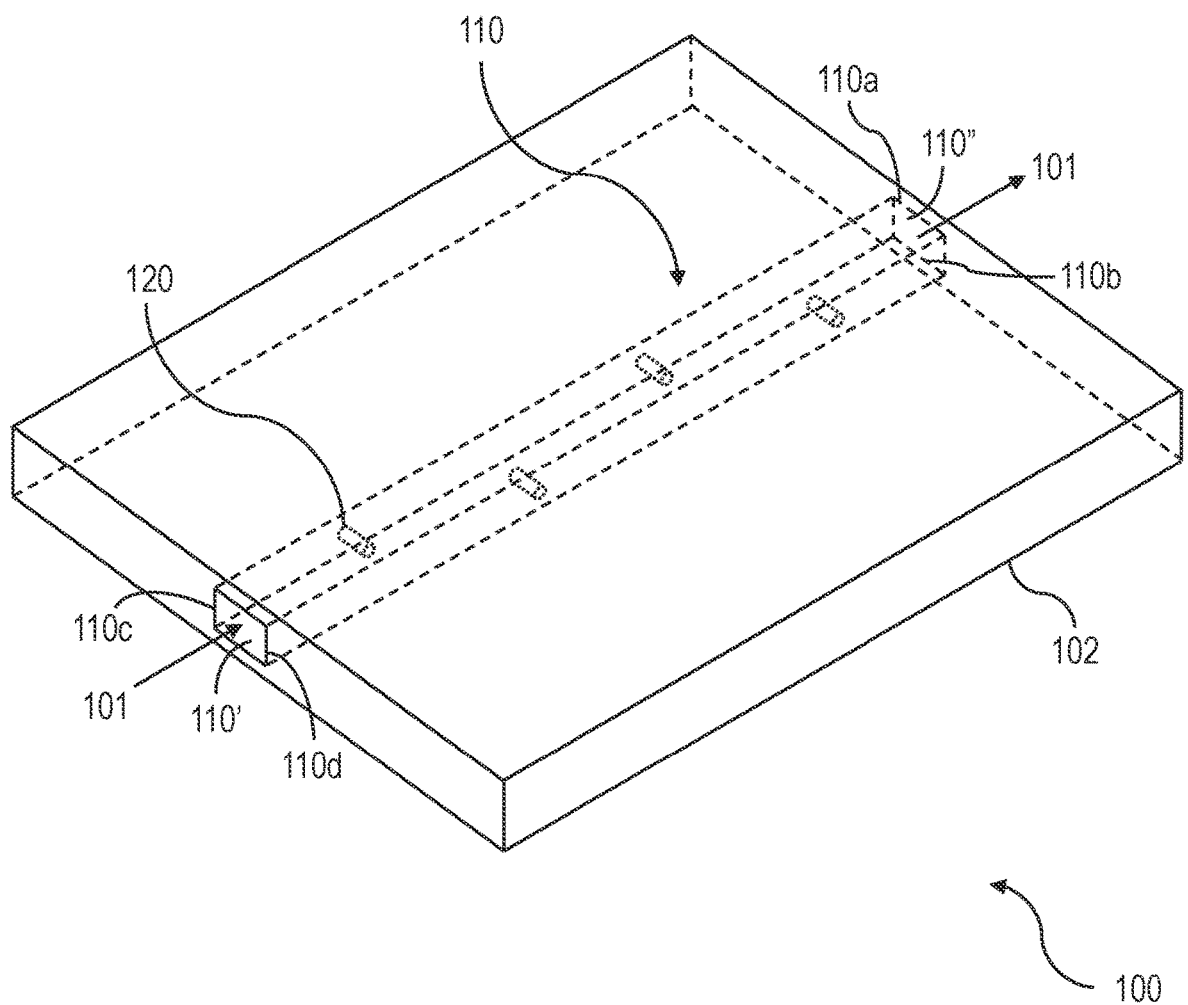
FIG. 1A is a schematic diagram of an example microfluidic device that can be used to detect hydrocarbon fuels in lubrication oils.

FIG. 1A depicts an example apparatus 100 constructed in accordance with the concepts herein. The apparatus 100 is a microfluidic apparatus that can be used to detect the presence of hydrocarbon fuel in a lubrication oil 101. The apparatus 100 includes a plate 102 that defines a microfluidic channel 110 configured to flow the lubrication oil 101. The microfluidic channel 110 includes an inlet 110' for receiving the lubrication oil 101. The microfluidic channel 110 includes an outlet 110" for discharging the lubrication oil 101. The plate 102 defines multiple walls of the microfluidic channel 110. For example, the plate 102 defines a top wall 110a, a bottom wall 110b opposite the top wall 110a, a first side wall 110c, and a second side wall 110d opposite the first side wall 110c. The walls 110a, 110b, 110c, 110d extend from the inlet 110' to the outlet 110".

The plate 102 can be made of any suitable material that is compatible with (that is, does not react with or degrade in response to exposure to) hydrocarbons, for example, silicon, glass, quartz, or polymethyl methacrylate (PMMA). The walls 110a, 110b, 110c, 110d are shaped for a small volume (for example, a sample) of lubrication oil 101 to flow through the microfluidic channel 110. In some implementations, the sample of lubrication oil 101 has a liquid volume in a range of from about 200 microliters (µL) to about 5 milliliters (mL). The lubrication oil 101 can, for example, be flowed through the microfluidic channel 110 at a rate in in a range of from about 0.1 milliliters per minute (mL/min) to about 10 mL, from about 0.2 mL/min to about 9 mL/min, from about 0.3 mL/min to about 8 mL/min, from about 0.4 mL/min to about 7 mL/min, or from about 0.5 mL/min to about 6 mL/min. In some implementations, the microfluidic channel 110 has a length (parallel to an overall direction of fluid flow of the lubrication oil 101 through the microfluidic channel 110, for example, the distance between the inlet 110' and the outlet 110") in a range of from about 10 centimeters (cm) to about 100 cm, from about 20 cm to about 90 cm, from about 30 cm to about 80 cm, from about 40 cm to about 70 cm, or from about 50 cm to about 60 cm. In some implementations, the microfluidic channel 110 has a width (for example, a distance between the first side wall 110c and the second side wall 110d) in a range of from about 1 millimeter (mm) to about 10 mm, from about 1 mm to about 9 mm, from about 1 mm to about 8 mm, from about 1 mm to about 7 mm, from about 1 mm to about 6 mm, or from about 1 mm to about 5 mm. In some implementations, the microfluidic channel 110 has a height (for example, a distance between the top wall 110a and the bottom wall 110b) in a range of from about 10 micrometers (µm) to about 1000 µm, from about 50 µm to about 900 µm, or from about 100 µm to about 800 µm.

The apparatus 100 includes micro-protrusion baffles 120 that are located within the microfluidic channel 110. The micro-protrusion baffles 120 are distributed between the inlet 110' and the outlet 110" of the microfluidic channel 110. The micro-protrusion baffles 120 can have any shape, for example, cylindrical, rectangular prism, or triangular prism. In some implementations, each micro-protrusion baffle 120 has a maximum dimension of at most 1 millimeter (that is, a maximum dimension of the respective micro-protrusion baffle 120 is 1 millimeter or shorter). In some implementations, each micro-protrusion baffle 120 has a minimum dimension of at least 10 micrometers (that is, a minimum dimension of the respective micro-protrusion baffle 120 is 10 micrometers or longer). For example, each of the dimensions (width, length, height) of the micro-protrusion baffles 120 are in a range of from 10 micrometers to 1 millimeter. In some implementations, each micro-protrusion baffle 120 has a length that is in a range of from 5 µm to about 500 µm, from about 10 µm to about 300 µm, or from about 10 µm to about 100 µm. In some implementations, each micro-protrusion baffle 120 has a width that is in a range of from 5 µm to about 500 µm, from about 10 µm to about 300 µm, or from about 10 µm to about 100 µm. In some implementations, each micro-protrusion baffle 120 has a height in a range of from about 10 µm to about 1000 µm, from about 50 µm to about 900 µm, or from about 100 µm to about 800 µm. Each micro-protrusion baffle 120 extends from any of the walls 110a, 110b, 110c, 110d. In some implementations, each micro-protrusion baffle 120 extends from any of the first side wall 110c or the second side wall 110d. In some implementations, the micro-protrusion baffles 120 alternate between extending from the first side wall 110c and extending from the second wall 110d in a direction from the inlet 110' to the outlet 110". In some implementations, each micro-protrusion baffle 120 has a free end that is a perpendicular distance (d) away from the respective side wall (110c or 110d) from which the baffle 120 extends that is in a range of from about 10 micrometers to about 100 micrometers. In some implementations, each of the micro-protrusion baffles 120 extend from the bottom wall 110b to the top wall 110a, such that each of the micro-protrusion baffles 120 span the height of the microfluidic channel 110.

Each micro-protrusion baffle 120 includes a cyclic olefin copolymer. The cyclic olefin copolymer is insoluble in acyclic (branched or unbranched) saturated hydrocarbons having a chemical formula of $C_nH_{2n+2}$ (paraffins), where n is an integer. Some examples of acyclic saturated hydrocarbons include methane, ethane, propane, butane, pentane, and hexane (and isomers thereof). The cyclic olefin copolymer is soluble in aromatic hydrocarbons, such as benzene, alkylbenzenes (for example, toluene and xylene), styrene, and naphthalene. In some implementations, the cyclic olefin copolymer is soluble in substituted aromatic hydrocarbons (that is, aromatic hydrocarbons that include substitutions of other elements, such as oxygen or nitrogen), such as aniline, phenol, and benzaldehyde.

In some implementations, each micro-protrusion baffle 120 is entirely made of the cyclic olefin copolymer, and the micro-protrusion baffles 120 are attached to any of the walls 110a, 110b, 110c, 110d. For example, the plate 102 and the micro-protrusion baffles 120 may be made of the cyclic olefin copolymer. In such cases, the plate 102 and the micro-protrusion baffles 120 (along with the microfluidic channel 110) can be formed simultaneously. In some implementations, a portion of the plate 102 (for example, the walls 110a, 110b, 110c, 110d of the microfluidic channel 110) are coated by a material that is compatible with hydrocarbons (for example, silicon, glass, quartz, or PMMA), so that the walls 110a, 110b, 110c, 110d are not affected by the sample of lubrication oil 101 even when hydrocarbons are present. For example, a patterned cyclic olefin copolymer can be made using carbon dioxide laser ablation to form the micro-protrusion baffles 120, which can be connected together with a rectangular ring. The structure (micro-protrusion baffles 120 and ring) can be attached to the microfluidic channel 110 (for example, made of polydimethylsiloxane (PDMS)) before curing.

In some implementations, the micro-protrusion baffles 120 and the walls 110a, 110b, 110c, 110d of the microfluidic channel 110 are made of the cyclic olefin polymer, and the microfluidic channel 110 is sandwiched by a material that is compatible with hydrocarbons (for example, silicon, glass, quartz, or PMMA) to form the plate 102. In such implementations, both the walls 110a, 110b, 110c, 110d and the micro-protrusion baffles 120 are affected when hydrocarbon fuels are present in the sample of lubrication oil 101.

In some implementations, each micro-protrusion baffle 120 is made of the same material as the plate 102, and the micro-protrusion baffles 120 are coated by the cyclic olefin copolymer. In some implementations, the micro-protrusion baffles 120 and the plate 102 are formed together by the same material (for example, silicon, glass, quartz, or PMMA) and then the walls 110a, 110b, 110c, 110d and the micro-protrusion baffles 120 are coated by the cyclic olefin copolymer. For example, the cyclic olefin copolymer can be dissolved in a solvent (such as toluene), and the solution (including solvent and dissolved cyclic olefin copolymer) can be spin-coated on the micro-protrusion baffles 120. The solvent can then be evaporated (for example, by a heater or by resting at room temperature), leaving behind the cyclic olefin copolymer as a coating on the micro-protrusion baffles 120.

Thus, the micro-protrusion baffles 120 are configured to at least partially dissolve in a presence of an aromatic hydrocarbon in the lubrication oil 101 flowed through the microfluidic channel 110. Dissolution of any of the micro-protrusion baffle 120 can indicate the presence of a hydrocarbon fuel (such as gasoline and diesel) in the lubrication oil 101. In some implementations, the plate 102 can also be made from a material (such as a cyclic olefin copolymer) that dissolves in the presence of an aromatic hydrocarbon, and in such implementations, dissolution of any of the walls 110a, 110b, 110c, 110d can indicate the presence of a hydrocarbon fuel in the lubrication oil 101. Although shown in FIG. 1A as including four micro-protrusion baffles 120, the apparatus 100 can include fewer micro-protrusion baffles 120 (for example, one micro-protrusion baffle 120, two micro-protrusion baffles 120, or three micro-protrusion baffles 120) or more micro-protrusion baffles 120 (for example, five micro-protrusion baffles 120 or more than five micro-protrusion baffles 120). In some cases, including three or more micro-protrusion baffles 120 may improve turbulence in the fluid flowing through the microfluidic channel 110. Increasing turbulence in the fluid flowing through the microfluidic channel 110 may, in some cases, accelerate dissolution of the micro-protrusion baffles 120. Increasing turbulence in the fluid flowing through the microfluidic channel 110 can also be useful, for example, in a cleaning process. For example, including additional micro-protrusion baffles 120 in the apparatus 100 can enhance turbulence in the cleaning solution (such as water) being used to clean the apparatus 100 after or before a test.

Figure 1B:
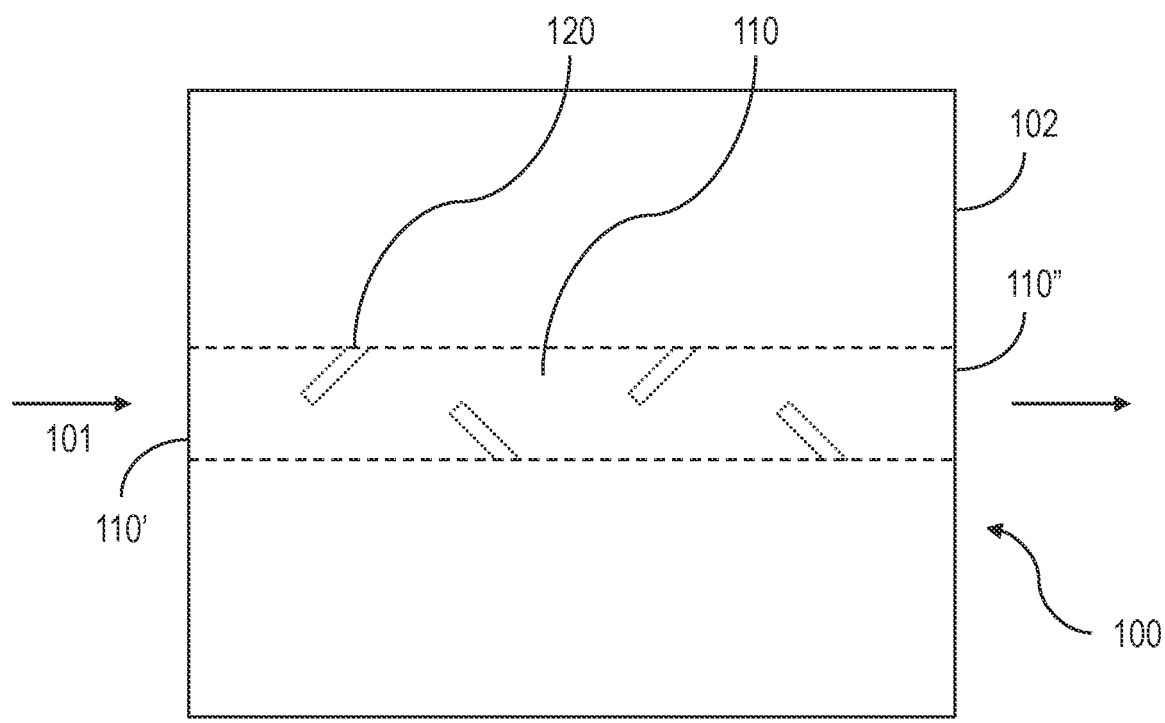
FIG. 1B is a schematic diagram of an example microfluidic device that can be used to detect hydrocarbon fuels in lubrication oils.
Figure 1C:
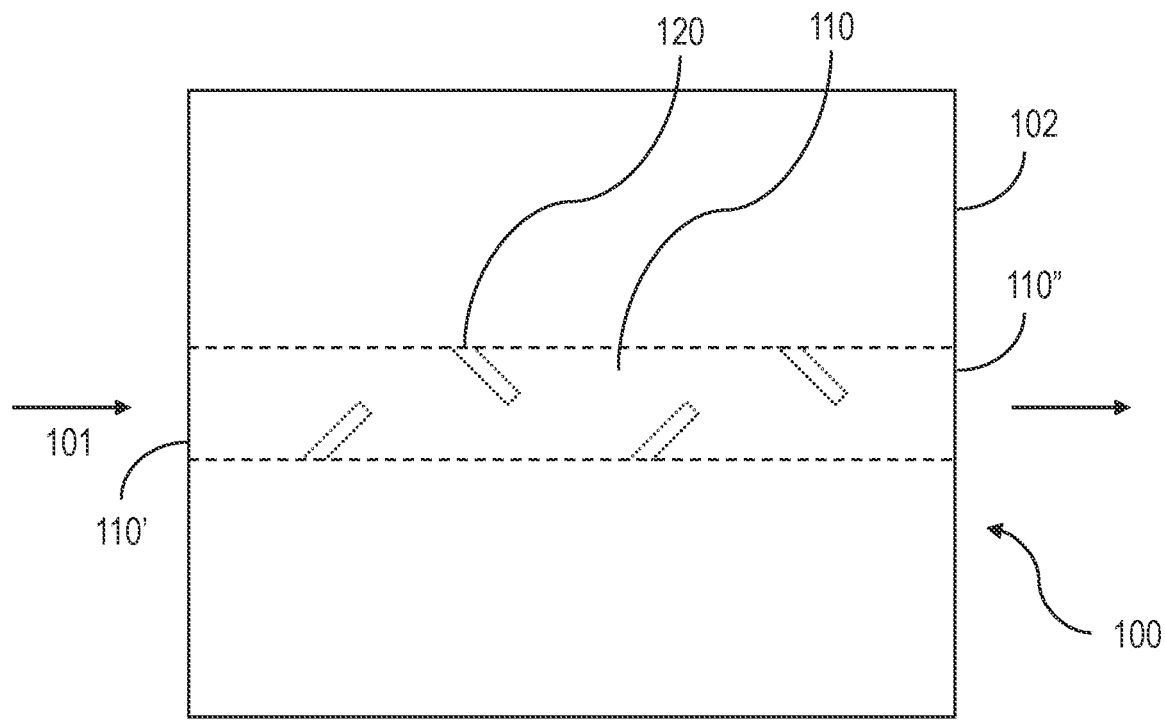
FIG. 1C is a schematic diagram of an example microfluidic device that can be used to detect hydrocarbon fuels in lubrication oils.

One or more of the micro-protrusion baffles 120 can extend perpendicularly from the first side wall 110c or the second side wall 110d. One or more of the micro-protrusion baffles 120 can extend non-perpendicularly from the first side wall 110c at a non-zero angle with respect to the first side wall 110c. One or more of the micro-protrusion baffles 120 can extend non-perpendicularly from the second side wall 110d at a non-zero angle with respect to the second side wall 110d. One or more of the micro-protrusion baffles 120 can extend toward the inlet 110'. FIG. 1B depicts an implementation of the apparatus 100 in which at least one of its micro-protrusion baffles 120 extends toward the inlet 110'. Having one or more micro-protrusion baffles 120 that extend toward the inlet 110' can, for example, make it easier to identify potential changes in size of the micro-protrusion baffles 120 (for example, due to dissolution). One or more of the micro-protrusion baffles 120 can extend toward the outlet 110". FIG. 1C depicts an implementation of the apparatus 100 in which at least one of its micro-protrusion baffles 120 extends toward the outlet 110". Having one or more micro-protrusion baffles 120 that extend toward the outlet 110" can, for example, mitigate or eliminate the potential of eddies and/or turbulence from forming in the lubrication oil 101 flowing through the microfluidic channel 110 and across the micro-protrusion baffles 120.

Figure 2:
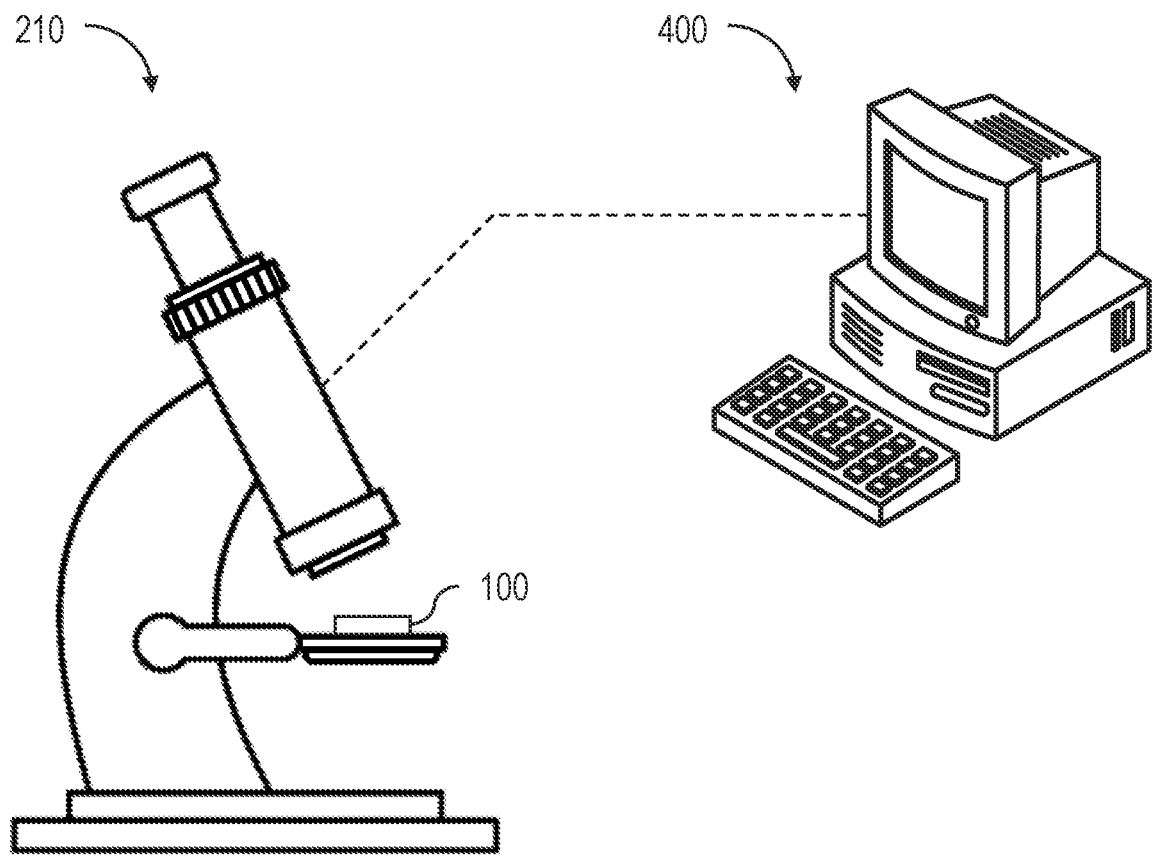
FIG. 2 is a schematic diagram of an example system that includes a microfluidic device for detecting hydrocarbon fuels in lubrication oils.

FIG. 2 depicts a system 200 that includes the apparatus 100. The system 200 includes a microscope 210 and a computer 400 that is communicatively coupled to the microscope 210. The microscope 210 can include a camera for capturing image/video data of the apparatus 100 as a sample of lubrication oil 101 flows through the microfluidic channel 110 of the plate 102. For example, the microscope 210 can be used to detect whether at least a portion of any of the micro-protrusion baffles 120 dissolve in response to the sample of lubrication oil 101 flowing through the microfluidic channel 110 and across the micro-protrusion baffles 120. In some cases, the micro-protrusion baffles 120 that are located more upstream (with respect to the general direction of fluid flow of the lubrication oil 101 from the inlet 110' to the outlet 110" through the microfluidic channel 110) may dissolve to a larger extent in comparison to those located more downstream. Complete or partial dissolution of any one of the micro-protrusion baffles 120 can indicate the presence of a hydrocarbon fuel in the lubrication oil 101. In some cases, all of the micro-protrusion baffles 120 undergoing partial or complete dissolution in response to the sample of lubrication oil 101 flowing across the micro-protrusion baffles 120 can indicate the presence of a hydrocarbon fuel in the lubrication oil 101. For example, if only one of the micro-protrusion baffles 120 appears to change in dimension and the remaining micro-protrusion baffles 120 remain intact in response to the sample of lubrication oil 101 flowing across the micro-protrusion baffle 120, this scenario may be indicative of a setup error in the test or erosion, as opposed to hydrocarbon fuel being present in the lubrication oil 101. In some cases, one or more of the micro-protrusion baffles 120 may dissolve to a larger extent in comparison to other micro-protrusion baffles 120. For example, the micro-protrusion baffle(s) 120 closer to the inlet 110' may dissolve more quickly than the micro-protrusion baffle(s) 120 closer to the outlet 110". The computer 400 can be used to control the microscope 210 (for example, record video and adjust a position of a camera of the microscope 210). The computer 400 is also shown in FIG. 4 and described in more detail later.

Figure 3:
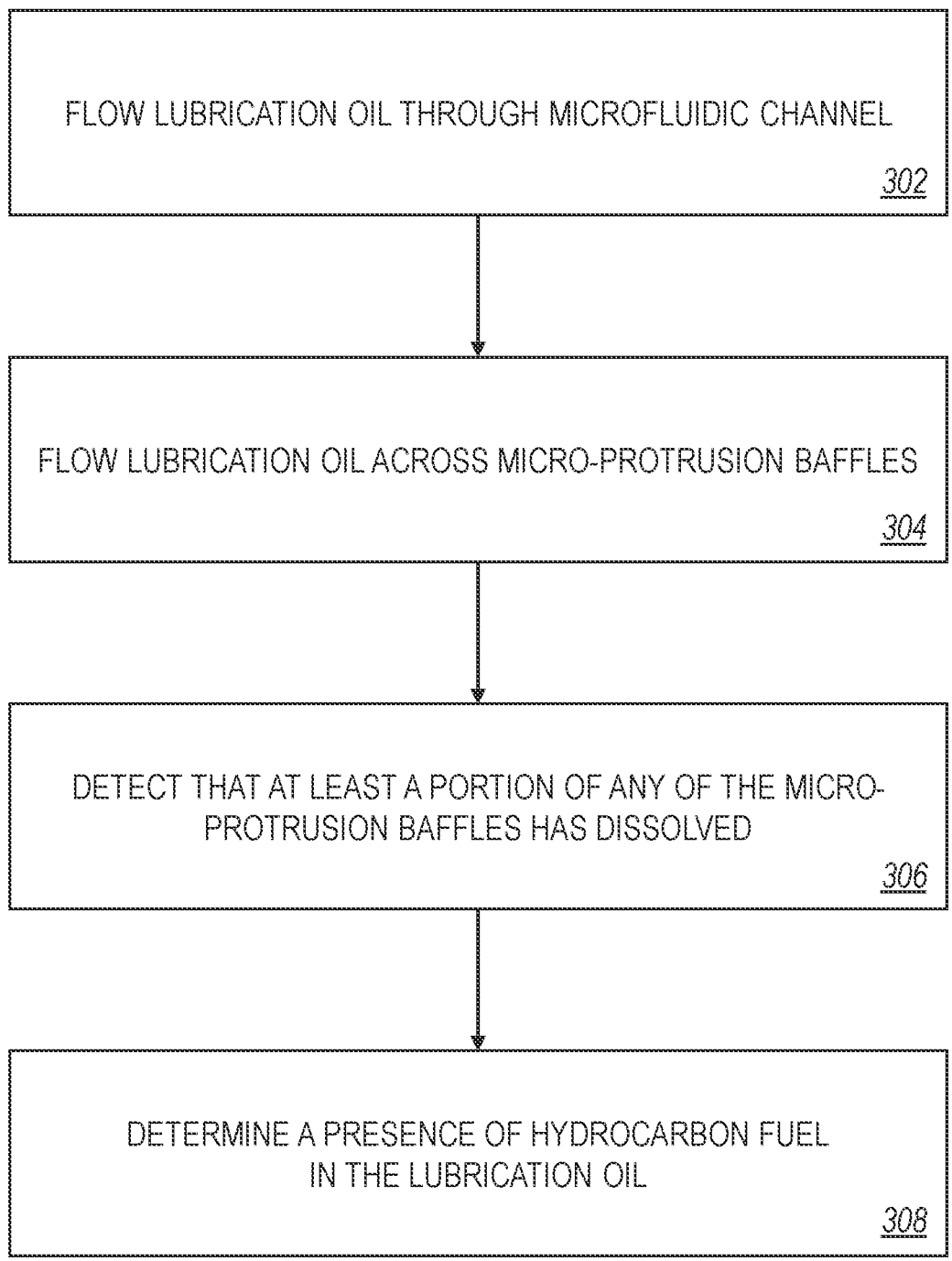
FIG. 3 is a flow chart of an example method for detecting hydrocarbon fuels in lubrication oils.

FIG. 3 is a flow chart of an example method 300 that can be implemented to detect the presence of hydrocarbon fuel in a lubrication oil (such as the lubrication oil 101). At block 302, a sample of lubrication oil (such as the lubrication oil 101) is flowed through a microfluidic channel (such as the microfluidic channel 110) defined by a plate (such as the plate 102). The microfluidic channel 110 has walls (such as walls 110a, 110b, 110c, 110d) that extend from an inlet (such as the inlet 110') to an outlet (such as the outlet 110") of the microfluidic channel 110. At block 304, the sample of lubrication oil 101 is flowed across micro-protrusion baffles (such as the micro-protrusion baffles 120) that are located within the microfluidic channel 110 and distributed between the inlet 110' and the outlet 110". Each micro-protrusion baffle 120 extend from any of the walls 110a, 110b, 110c, 110d. Each micro-protrusion baffle 120 includes a cyclic olefin copolymer. At block 306, it is detected that at least a portion of any of the micro-protrusion baffles 120 has dissolved in response to the sample of lubrication oil 101 flowing across the micro-protrusion baffles 120 at block 304. The microscope 210 and the computer 400 can be used to detect dissolution of the micro-protrusion baffles 120 at block 306. For example, the microscope 210 can capture image/video data while the sample of lubrication oil 101 is flowed through the microfluidic channel 110 (block 302) and across the micro-protrusion baffles 120 (at block 304). The dimensions of the micro-protrusion baffles 120 can be measured and tracked, for example, by analysis of the image/video data by the computer 400. If any of the dimensions of the micro-protrusions baffles 120 change (for example, decrease as a result of dissolution), this may be indicative of the presence of a hydrocarbon fuel in the lubrication oil 101. At block 308, a presence of hydrocarbon fuel in the sample of lubrication oil 101 is determined based on detecting that at least a portion of any of the micro-protrusion baffles 120 has dissolved at block 306.

In some implementations, a second sample of lubrication oil 101 is flowed through the microfluidic channel 110. The second sample of lubrication oil 101 can be flowed across the micro-protrusion baffles 120. It can be detected that not even a portion of the micro-protrusion baffles 120 has dissolved in response to the second sample of lubrication oil 101 flowing across the micro-protrusion baffles 120. An absence of hydrocarbon fuel in the second sample of lubrication oil 101 can be determined based on detecting that not even a portion of the micro-protrusion baffles 120 has dissolved.

Figure 4:
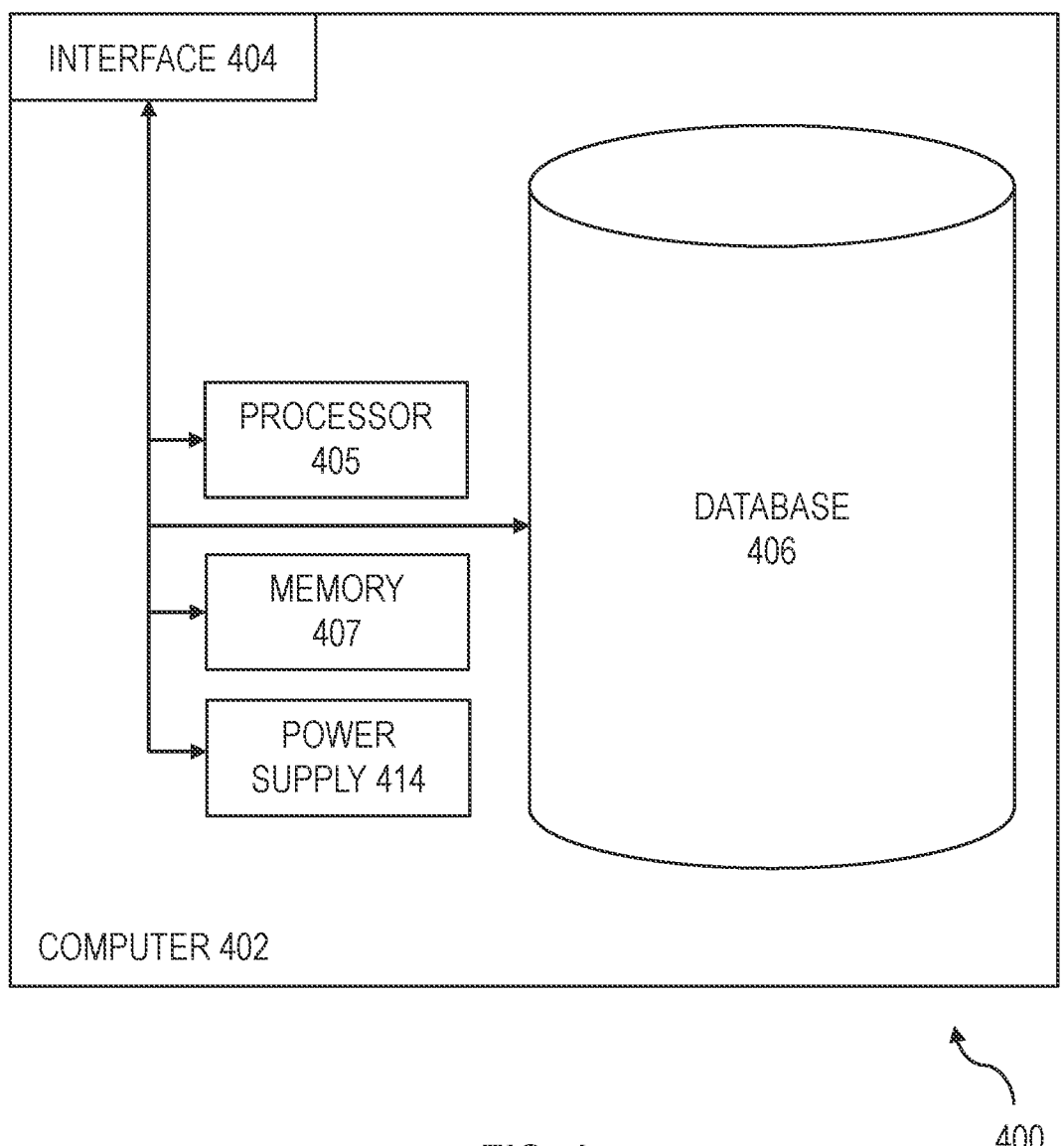
FIG. 4 is a schematic diagram of an example computer.

FIG. 4 is a block diagram of an example computer system 400 used to provide computational functionalities associated with described algorithms, methods, functions, processes, flows, and procedures, as described in this specification, according to an implementation. The illustrated computer 402 is intended to encompass any computing device such as a server, desktop computer, laptop/notebook computer, one or more processors within these devices, or any other processing device, including physical or virtual instances (or both) of the computing device. Additionally, the computer 402 can include a computer that includes an input device, such as a keypad, keyboard, touch screen, or other device that can accept user information, and an output device that conveys information associated with the operation of the computer 402, including digital data, visual, audio information, or a combination of information.

The computer 402 includes an interface 404. Although illustrated as a single interface 404 in FIG. 4, two or more interfaces 404 may be used according to particular needs, desires, or particular implementations of the computer 402. Although not shown in FIG. 4, the computer 402 can be communicably coupled with a network. The interface 404 is used by the computer 402 for communicating with other systems that are connected to the network in a distributed environment. Generally, the interface 404 comprises logic encoded in software or hardware (or a combination of software and hardware) and is operable to communicate with the network. More specifically, the interface 404 may comprise software supporting one or more communication protocols associated with communications such that the network or interface's hardware is operable to communicate physical signals within and outside of the illustrated computer 402. The interface 404 can include a control interface, which can be used to couple the computer 402 to controls. In some implementations, the control interface is a bank of relays, a bank of MOSFET power controllers, a serial peripheral interface (SPI), or a Fieldbus, and the like. The interface 404 can include a sensor interface, which can be used to couple the computer 402 to sensors. In some implementations, the sensor interface is a bank of analog-to-digital converters (ADCs), and I2C bus, a serial peripheral interface (SPI) bus, or a Fieldbus, and the like. The interface 404 can include a human machine interface, which can be used by a user to interact with the computer 402. In some implementations, the human machine interface includes a monitor or a touch screen that is configured to display information, for example, to a user.

The computer 402 includes a processor 405. The processor 405 may be a microprocessor, a multi-core processor, a multithreaded processor, an ultra-low-voltage processor, an embedded processor, or a virtual processor. In some embodiments, the processor 405 may be part of a system-on-a-chip (SoC) in which the processor 405 and the other components of the computer 402 are formed into a single integrated electronics package. In some implementations, the processor 405 may include processors from Intel® Corporation of Santa Clara, California, from Advanced Micro Devices, Inc. (AMD) of Sunnyvale, California, or from ARM Holdings, LTD., Of Cambridge, England. Any number of other processors from other suppliers may also be used. Although illustrated as a single processor 405 in FIG. 4, two or more processors may be used according to particular needs, desires, or particular implementations of the computer 402. Generally, the processor 405 executes instructions and manipulates data to perform the operations of the computer 402 and any algorithms, methods, functions, processes, flows, and procedures as described in this specification. The processor 405 may communicate with other components of the computer 402 over a bus. The bus may include any number of technologies, such as industry standard architecture (ISA), extended ISA (EISA), peripheral component interconnect (PCI), peripheral component interconnect extended (PCIx), PCI express (PCIe), or any number of other technologies. The bus may be a proprietary bus, for example, used in an SoC based system. Other bus technologies may be used, in addition to, or instead of, the technologies above.

The computer 402 can also include a database 406 that can hold data for the computer 402 or other components (or a combination of both) that can be connected to the network. Although illustrated as a single database 406 in FIG. 4, two or more databases (of the same or combination of types) can be used according to particular needs, desires, or particular implementations of the computer 402 and the described functionality. While database 406 is illustrated as an integral component of the computer 402, database 406 can be external to the computer 402. The database 406 can be used for the persistent storage of information, such as data, applications, operating systems, and so forth. The database 406 may be a nonvolatile RAM, a solid-state disk drive, or a flash drive, among others. In some implementations, the database 306 will include a hard disk drive, such as a micro hard disk drive, a regular hard disk drive, or an array of hard disk drives, for example, associated with a DCS or a cloud server.

The computer 402 also includes a memory 407 that can hold data for the computer 402 or other components (or a combination of both) that can be connected to the network. Although illustrated as a single memory 407 in FIG. 4, two or more memories 407 (of the same or combination of types) can be used according to particular needs, desires, or particular implementations of the computer 402 and the described functionality. While memory 407 is illustrated as an integral component of the computer 402, memory 407 can be external to the computer 402. The memory 407 can be a transitory or non-transitory storage medium. In some implementations, such as in PLCs and other process control units, the memory 407 is integrated with the database 406 used for long-term storage of programs and data. The memory 407 can include any number of volatile and non-volatile memory devices, such as volatile random-access memory (RAM), static random-access memory (SRAM), flash memory, and the like. In smaller devices, such as PLCs, the memory 407 may include registers associated with the processor 405 itself.

The memory 407 stores computer-readable instructions executable by the processor 405 that, when executed, cause the processor 405 to perform operations, such as adjust a position of a camera of the microscope 210, cause the camera of the microscope 210 to capture image/video data, receive and store image/video data from the microscope 210, and analyze image/video data from the microscope 210 to determine a change in size (for example, due to dissolution) of the micro-protrusion baffles 120. The computer 402 can also include a power supply 414. The power supply 414 can include a rechargeable or non-rechargeable battery that can be configured to be either user- or non-user-replaceable. The power supply 414 can be hard-wired. There may be any number of computers 402 associated with, or external to, a computer system containing computer 402, each computer 402 communicating over the network. Further, the term "client," "user," "operator," and other appropriate terminology may be used interchangeably, as appropriate, without departing from this specification. Moreover, this specification contemplates that many users may use one computer 402, or that one user may use multiple computers 402.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

As used in this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described components and systems can generally be integrated together or packaged into multiple products.

Accordingly, the previously described example implementations do not define or constrain the present disclosure. Other changes, substitutions, and alterations are also possible without departing from the spirit and scope of the present disclosure.

What is claimed is:

1. A microfluidic apparatus comprising:
a plate defining a microfluidic channel configured to flow lubrication oil, the microfluidic channel having an inlet for receiving the lubrication oil and an outlet for discharging the lubrication oil, the plate defining a plurality of walls of the microfluidic channel, the plurality of walls extending from the inlet to the outlet; and
a plurality of micro-protrusion baffles located within the microfluidic channel and distributed between the inlet and the outlet, each micro-protrusion baffle extending from any of the plurality of walls, each micro-protrusion baffle comprising a cyclic olefin copolymer that is insoluble in acyclic saturated hydrocarbons, each micro-protrusion baffle configured to at least partially dissolve in a presence of an aromatic hydrocarbon in the lubrication oil flowed through the microfluidic channel.

2. The apparatus of claim 1, wherein the plurality of walls comprises a top wall, a bottom wall opposite the top wall, a first side wall, and a second side wall opposite the first side wall, and each of the plurality of micro-protrusion baffles extend from any of the first side wall or the second side wall.

3. The apparatus of claim 2, wherein each micro-protrusion baffle extends from the bottom wall to the top wall.

4. The apparatus of claim 2, wherein each micro-protrusion baffle comprises a free end that is a perpendicular distance, from the respective side wall from which the respective micro-protrusion baffle extends, that is in a range of from about 10 micrometers to about 100 micrometers.

5. The apparatus of claim 2, wherein the plurality of micro-protrusion baffles, in a direction from the inlet to the outlet, alternate between extending from the first side wall and extending from the second side wall.

6. The apparatus of claim 2, wherein at least one of the plurality of micro-protrusion baffles extends perpendicularly from the first side wall.

7. The apparatus of claim 2, wherein each micro-protrusion baffle has a maximum dimension that is less than 1 millimeter.

8. The apparatus of claim 2, wherein at least one of the plurality of micro-protrusion baffles extends from the first side wall non-perpendicularly at a non-zero angle with respect to the first side wall.

9. The apparatus of claim 8, wherein the at least one of the plurality of micro-protrusion baffles extends toward the outlet.

10. The apparatus of claim 8, wherein the at least one of the plurality of micro-protrusion baffles extends toward the inlet.

11. A method comprising:
flowing a sample of lubrication oil through a microfluidic channel defined by a plate, the microfluidic channel having a plurality of walls extending from an inlet to an outlet of the microfluidic channel;
flowing the sample of lubrication oil across a plurality of micro-protrusion baffles located within the microfluidic channel and distributed between the inlet and the outlet, each of the plurality of micro-protrusion baffles extending from any of the plurality of walls, each of the plurality of micro-protrusion baffles comprising a cyclic olefin copolymer;
detecting that at least a portion of any of the plurality of micro-protrusion baffles has dissolved in response to the sample of lubrication oil flowing across the plurality of micro-protrusion baffles; and
determining a presence of hydrocarbon fuel in the sample of lubrication oil based on detecting that at least a portion of any of the plurality of micro-protrusion baffles has dissolved.

12. The method of claim 11, wherein the plurality of walls comprises a top wall, a bottom wall opposite the top wall, a first side wall, and a second side wall opposite the first side wall, and each of the plurality of micro-protrusion baffles extend from any of the first side wall or the second side wall.

13. The method of claim 12, wherein each of the plurality of micro-protrusion baffles extend from the bottom wall to the top wall.

14. The method of claim 12, wherein each of the plurality of micro-protrusion baffles extend from any of the first side wall or the second side wall by a perpendicular distance from the respective side wall in a range of from about 10 micrometers to about 100 micrometers.

15. The method of claim 12, wherein the plurality of micro-protrusion baffles, in a direction from the inlet to the outlet, alternate between extending from the first side wall and extending from the second side wall.

16. The method of claim 12, wherein at least one of the plurality of micro-protrusion baffles extends perpendicularly from the first side wall.

17. The method of claim 12, wherein at least one of the plurality of micro-protrusion baffles extends from the first side wall non-perpendicularly at a non-zero angle with respect to the first side wall.

18. The method of claim 12, comprising:
flowing a second sample of lubrication oil through the microfluidic channel;
flowing the second sample of lubrication oil across the plurality of micro-protrusion baffles;
detecting that the plurality of micro-protrusion baffles has not dissolved in response to the second sample of lubrication oil flowing across the plurality of micro-protrusion baffles; and
determining an absence of hydrocarbon fuel in the second sample of lubrication oil based on detecting that the plurality of micro-protrusion baffles has not dissolved.

19. An apparatus comprising:
- a plate defining a microfluidic channel configured to flow a sample of lubrication oil, the microfluidic channel having an inlet for receiving the sample of lubrication oil and an outlet for discharging the sample of lubrication oil, the plate defining a plurality of walls of the microfluidic channel, the plurality of walls extending from the inlet to the outlet; and
- a micro-protrusion baffle located within the microfluidic channel between the inlet and the outlet, the micro-protrusion baffle extending from any of the plurality of walls, the micro-protrusion baffle comprising a cyclic olefin copolymer, wherein dissolution of at least a portion of the micro-protrusion baffle in response to the sample of lubrication oil flowing through the microfluidic channel indicates a presence of hydrocarbon fuel in the sample of lubrication oil.

20. The apparatus of claim 19, wherein the micro-protrusion baffle has a maximum dimension that is less than 1 millimeter and extends perpendicularly from one of the plurality of walls.

* * * * *